US00PP28431P2

(12) United States Plant Patent
Delabroye

(10) Patent No.: US PP28,431 P2
(45) Date of Patent: Sep. 19, 2017

(54) ***HEUCHERA* PLANT NAMED 'CARMENCITA'**

(50) Latin Name: ***Heuchera* hybrid**
Varietal Denomination: Carmencita

(71) Applicant: Thierry Delabroye, Hantay (FR)

(72) Inventor: Thierry Delabroye, Hantay (FR)

(73) Assignee: SANDRINE DELABROYE, Hantay (FR)

( * ) Notice: Subject to any disclaimer, the term of this patent is extended or adjusted under 35 U.S.C. 154(b) by 40 days.

(21) Appl. No.: 14/998,568

(22) Filed: Jan. 19, 2016

(51) Int. Cl.
*A01H 5/12* (2006.01)

(52) U.S. Cl.
USPC ..... Plt./440

(58) Field of Classification Search
USPC ..... Plt./440
See application file for complete search history.

*Primary Examiner* — June Hwu
(74) *Attorney, Agent, or Firm* — Penny J. Aguirre

(57) ABSTRACT

A new cultivar of hybrid *Heuchera* named 'Carmencita' that is characterized by its floriferous blooming habit, its long flowering period, its compact plant habit, its good sun tolerance with very little to no scorching observed and its foliage that is red-purple in color with a glossy surface.

2 Drawing Sheets

Botanical classification: *Heuchera* hybrid.
Cultivar designation: 'Carmencita'.

BACKGROUND OF THE INVENTION

The present invention relates to a new and distinct cultivar of *Heuchera* of hybrid origin, botanically known as a *Heuchera* and is hereinafter referred to by its cultivar name 'Carmencita'.

The new cultivar arose from an ongoing breeding program conducted by the Inventor at his nursery in Hantay, France. The objectives of the breeding program were to select cultivars that were floriferous with distinct foliage coloration. The new cultivar was discovered as a chance seedling in a trial plot in March of 2013. The trial plot contained hundreds of cultivars and proprietary seedlings of *Heuchera* from the Inventor's breeding program. The parentage of 'Carmencita' is therefore unknown.

Asexual propagation of the new cultivar was first accomplished under the direction of the Inventor by in vitro propagation of meristem tissue in Rijswijk, The Netherlands in in April of 2014. Asexual propagation of the new cultivar by stem cuttings and in vitro propagation has shown that the unique features are stable and reproduced true to type in successive generations.

SUMMARY OF THE INVENTION

The following traits have been repeatedly observed and represent the characteristics of the new cultivar. These attributes in combination distinguish 'Carmencita' as a new and unique cultivar of *Heuchera*.

1. 'Carmencita' exhibits a very floriferous blooming habit.
2. 'Carmencita' exhibits a long flowering period.
3. 'Carmencita' exhibits a compact plant habit.
4. 'Carmencita' exhibits good sun tolerance with very little to no scorching observed.
5. 'Carmencita' exhibits foliage that is red-purple in color with a glossy surface.

'Carmencita' can be most closely compared to the *Heuchera* cultivars 'Beujolais' (U.S. Plant Pat. No. 19,577) and 'Pink Pearls' (U.S. Plant Pat. No. 27,530). 'Beujolais' is similar to 'Carmencita' in having foliage that has similar red colorations. 'Beujolais' differs from 'Carmencita' in having foliage that has mottled silver coloration and in having a much less floriferous blooming habit. 'Pink Pearls' is similar to 'Carmencita' in having a floriferous blooming habit and in having a long flowering period. 'Pink Pearls' differs from 'Carmencita' in having flowers that are smaller in size.

BRIEF DESCRIPTION OF THE DRAWINGS

The accompanying colored photographs illustrate the overall appearance and distinct characteristics of the new *Heuchera*. The photographs were taken of a plant 18-months in age as grown in a poly covered greenhouse in a 25-cm container in Hantay, France.

The photograph in FIG. 1 provides a side view of the plant habit of 'Carmencita' in bloom.

Figure 1:
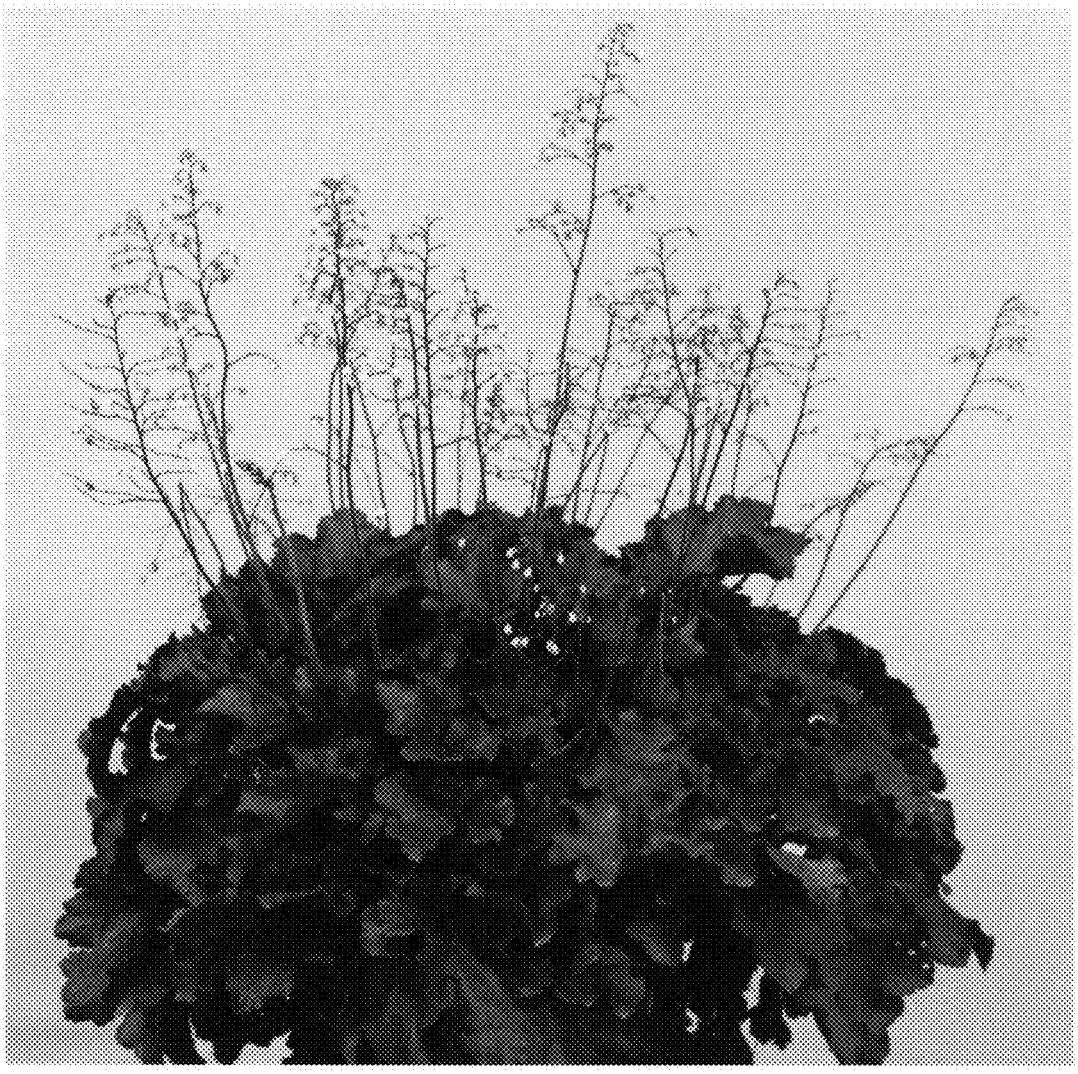
Figure 2:
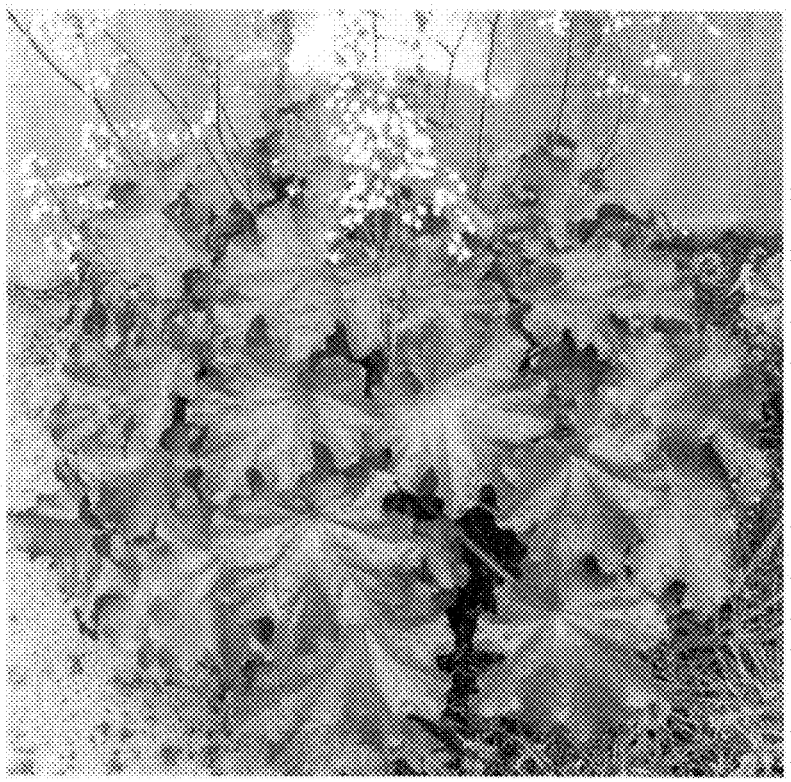

The photograph in FIG. 2 provides a view of the spring foliage of 'Carmencita'.

Figure 3:
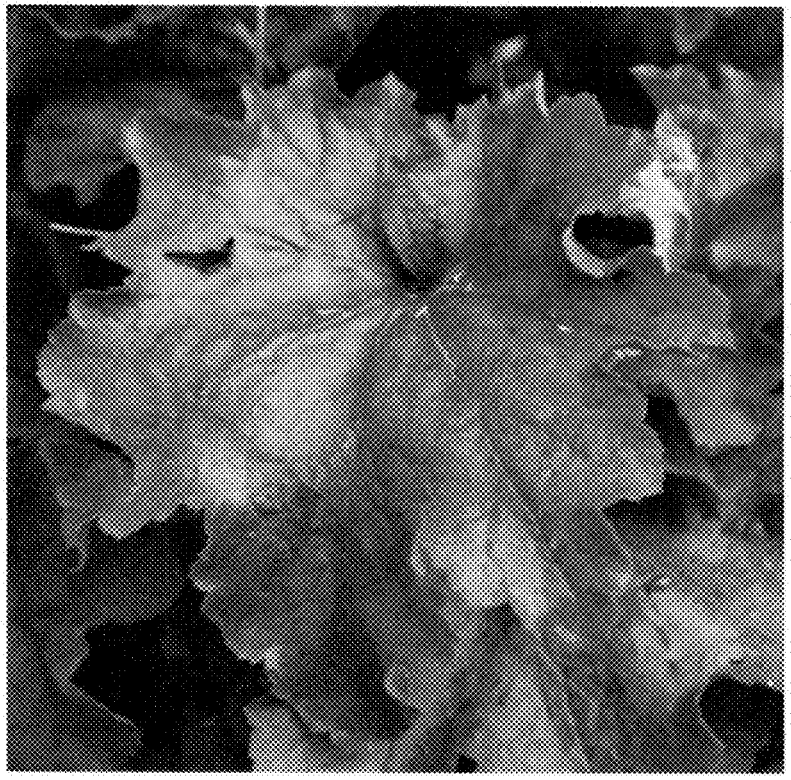

The photograph in FIG. 3 provides a close-up view of a leaf in summer of 'Carmencita'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 18 month-old plants of the new cultivar as grown in a poly covered greenhouse in 25-cm containers in Hantay, France. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—An average of 4 weeks in late spring to early autumn in France.

*Plant type*.—Herbaceous perennial.

*Plant habit*.—Compact, clump-forming, mounded foliage.

*Height and spread*.—Average of 31 cm in height from soil to top of leaves and 62.9 cm from soil to top of inflorescences and 66.5 cm in width.

*Hardiness*.—At least in U.S.D.A. Zones 3 to 9.

*Diseases and pests*.—Not susceptibility or resistance to diseases and pests has been observed.

*Environmental stresses*.—Good sun tolerant with very little to no scorching observed.

*Root description*.—Fibrous roots on woody rootstalks, 163B in color.

*Branching habit*.—Flowering stem emerge from basal rosettes, no lateral branches.

*Propagation*.—In vitro propagation is the preferred method, stem cuttings and division are also possible.

*Growth rate*.—Moderately vigorous.

Stem description (peduncle, flowering stem):

*Shape*.—Round.

*Stem color*.—N186D.

*Stem size*.—An average of 3.5 mm in diameter and 50 cm in length.

*Stem strength*.—Moderately strong.

*Stem aspect*.—Flowering stems grow in an average angle of 70° to soil level (0°=horizontal).

*Stem surface*.—Moderately glossy, densely covered with soft pubescence, average of 0.75 mm in length, N186D in color.

*Stem number*.—Average of 22 flowering stems.

Foliage description:

*Leaf shape*.—Orbicular to broad ovate.

*Leaf division*.—Simple.

*Leaf base*.—Hastate, moderately to strongly overlapping.

*Leaf apex*.—Obtuse, outer tip very short mucronate.

*Leaf venation*.—Laciniate, upper vein color; young leaves in between N199B to 200D, mature leaves 147A, lower vein color; young leaves in between N186D to 187D, mature leaves N186C.

*Leaf margins*.—Lobed with average of 7 lobes per leaf, lobe margins bi-crenate.

*Leaf attachment*.—Petiolate.

*Leaf arrangement*.—Alternate, basal rosettes.

*Leaf orientation*.—Typically nearly horizontal to petiole and slightly cupped.

*Leaf surface*.—Upper side moderately glossy, lower side very slightly glossy, both sides moderately covered with short strigose hairs an average length of 0.8 mm and 155A in color.

*Leaf color*.—Young upper surface; 185A and 187C, young lower surface; 187D, mature upper surface; N199B to 200D, older leaves 147A, mature lower surface; between N186D to 187C, older leaves N186C.

*Leaf size*.—Average of 13.5 cm in length and 13.2 cm in width.

*Leaf quantity*.—31 per basal rosette.

*Petioles*.—Average of 20.1 cm in length and 4 mm in width, color N186C, surface covered with dense soft pubescence, average of 2 mm in length and 155A in color.

*Bracts*.—One at the base of each leaf, linear-subulate in shape, narrow acute apex, with an average of 2.1 cm in length and 8 mm in width, N186D in color.

Flower description:

*Inflorescence type*.—Numerous small bell-shaped flowers arranged on pyramidal panicles on flower scapes emerging from the base of the rosette.

*Inflorescence size*.—An average of 24.7 cm in height (excluding peduncle; measured from lowest flower to top), average of 51.1 cm in height from base of peduncle to top and 10.7 cm in width.

*Inflorescence number*.—An average of 15.

*Flower fragrance*.—None.

*Flower arrangement*.—Axillary panicle.

*Flower quantity*.—Average of 750 flowers per flowering stem.

*Flower lastingness*.—Average of one week, self cleaning.

*Flower buds*.—Obovate in shape, an average of 3 mm in diameter and 5 mm in length, 62A to 63C, top is 69D in color.

*Flower aspect*.—Outward to slightly nodding.

*Flower type*.—Campanulate.

*Flower size*.—About 7 mm in depth and diameter.

*Petals*.—About 5, rotate arrangement and implanted in the hypanthium at base, oblanceolate in shape, margin is entire, apex is acute, upper and lower surface is matte and glabrous, color of upper and lower surface when opening and fully open; NN155D, not fading, average of 4 mm in length and 1 mm in width.

*Calyx*.—Campanulate, sepals fused to hypanthium, 6 mm in length and 5.5 mm in diameter.

*Sepals*.—5, fused, campanulate hypanthium, oblong in shape, average of 6 mm in length and 1.75 mm in width, margin is entire, apex is obtuse, fused base, surfaces are matte, outer side is moderately covered with very short glandular hairs 0.25 mm in length and between 62A to 62B in color, color: immature and mature upper surface; 69C, base is 68C to 68D, immature and mature lower surface; 62A to 63C.

*Pedicels*.—Average of 4 mm in length and 0.5 mm in diameter, 184C to 184D in color, moderate strength, average angle of 45° (0°=horizontal).

Reproductive organs:

*Gynoecium*.—Pistils; 2, 4 mm in length, stigma; is pointed in shape, N155D in color, styles; 3.75 mm in length and N155D in color, ovaries; 155A in color.

*Androcoecium*.—Average of 5 stamens, anthers; ovate in shape, average of 0.5 mm in length and 169D in color, filament; 2.5 mm in length and NN155D in color, pollen is low in quantity and 170C to 170D in color.

*Seed/fruit*.—No fruit or seeds were observed.

It is claimed:

1. A new and distinct cultivar of hybrid *Heuchera* plant named 'Carmencita' as herein illustrated and described.

* * * * *